United States Patent
Tockman et al.

(10) Patent No.: US 7,974,709 B2
(45) Date of Patent: Jul. 5, 2011

(54) GUIDE WIRE STYLET

(75) Inventors: Bruce A. Tockman, Scandia, MN (US); Frank Vandeputte, Hoeilaart (BE); Muralidharan Srivathsa, Shoreview, MN (US); Randy Westlund, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 12/564,731

(22) Filed: Sep. 22, 2009

(65) Prior Publication Data

US 2010/0010608 A1 Jan. 14, 2010

Related U.S. Application Data

(62) Division of application No. 11/432,950, filed on May 12, 2006, now Pat. No. 7,610,105, which is a division of application No. 10/675,932, filed on Sep. 30, 2003, now Pat. No. 7,174,222.

(51) Int. Cl.
*A61N 1/00* (2006.01)

(52) U.S. Cl. .................................................. 607/122

(58) Field of Classification Search .......... 607/122–128; 600/481; 439/668; 623/1.11; 606/213
See application file for complete search history.

(56) References Cited

U.S. PATENT DOCUMENTS

| | | | |
|---|---|---|---|
| 4,798,211 A | 1/1989 | Goor et al. | |
| 4,867,173 A | 9/1989 | Leoni | |
| 5,238,005 A | 8/1993 | Imran | |
| 5,916,178 A | 6/1999 | Noone et al. | |
| 5,989,210 A | 11/1999 | Morris et al. | |
| 6,102,942 A | 8/2000 | Ahari | |
| 6,500,130 B2 | 12/2002 | Kinsella et al. | |
| 6,592,581 B2 | 7/2003 | Bowe | |
| 6,616,684 B1 * | 9/2003 | Vidlund et al. | 606/213 |
| 6,706,018 B2 * | 3/2004 | Westlund et al. | 604/194 |
| 6,723,073 B2 | 4/2004 | Ley et al. | |
| 6,755,694 B2 | 6/2004 | Ries et al. | |

OTHER PUBLICATIONS

Notice of Allowance dated Sep. 7, 2006 from U.S. Appl. No. 10/675,932, 6 pages.
Office Action Response dated May 15, 2006 from U.S. Appl. No. 10/675,932, 10 pages.
Office Action dated Apr. 11, 2006 from U.S. Appl. No. 10/675,932, 7 pages.
Notice of Allowance dated Jun. 15, 2009 from U.S. Appl. No. 11/432,950, 6 pages.
Office Action Response dated Mar. 19, 2009 from U.S. Appl. No. 11/432,950, 12 pages.
Office Action dated Jan. 23, 2009 from U.S. Appl. No. 11/432,950, 6 pages.
Office Action Response dated Sep. 22, 2008 from U.S. Appl. No. 11/432,950, 10 pages.
Interview Summary dated Sep. 4, 2008 from U.S. Appl. No. 11/432,950, 4 pages.
Office Action dated Apr. 17, 2008 from U.S. Appl. No. 11/432,950, 5 pages.

* cited by examiner

*Primary Examiner* — George Manuel
(74) *Attorney, Agent, or Firm* — Hollingsworth & Funk, LLC

(57) ABSTRACT

A cardiac lead system includes a cardiac lead having a lumen, and a guide member displaceable within the lumen. The guide member includes a guide wire extension that extends distal to the elongated body of the guide member. The guide wire extension is dimensioned to pass through an external distal opening of the cardiac lead lumen. Engagement of stop features or a stop mechanism of the cardiac lead system provides a push point for advancing the cardiac lead system through the patient's anatomy.

20 Claims, 14 Drawing Sheets

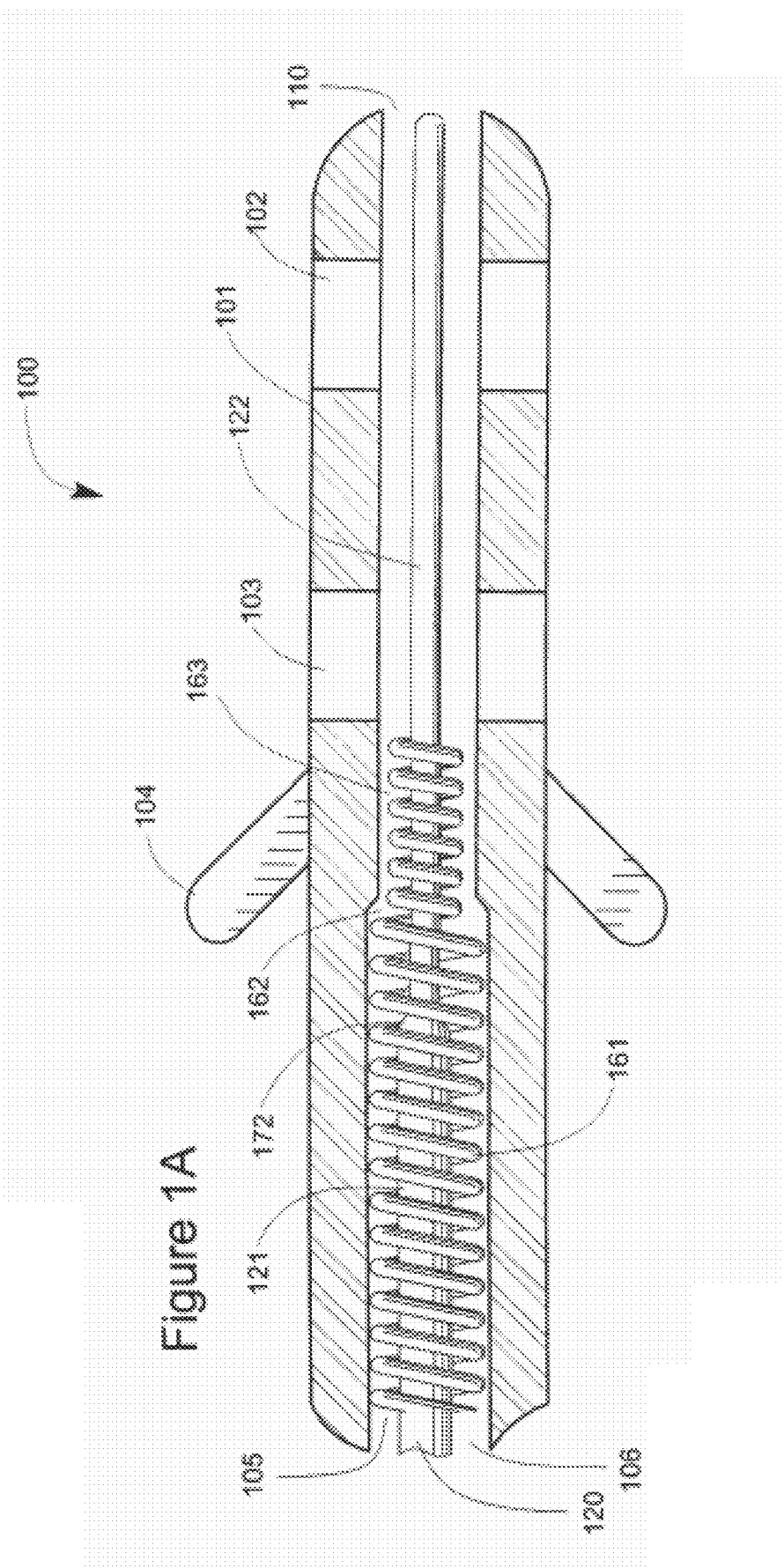

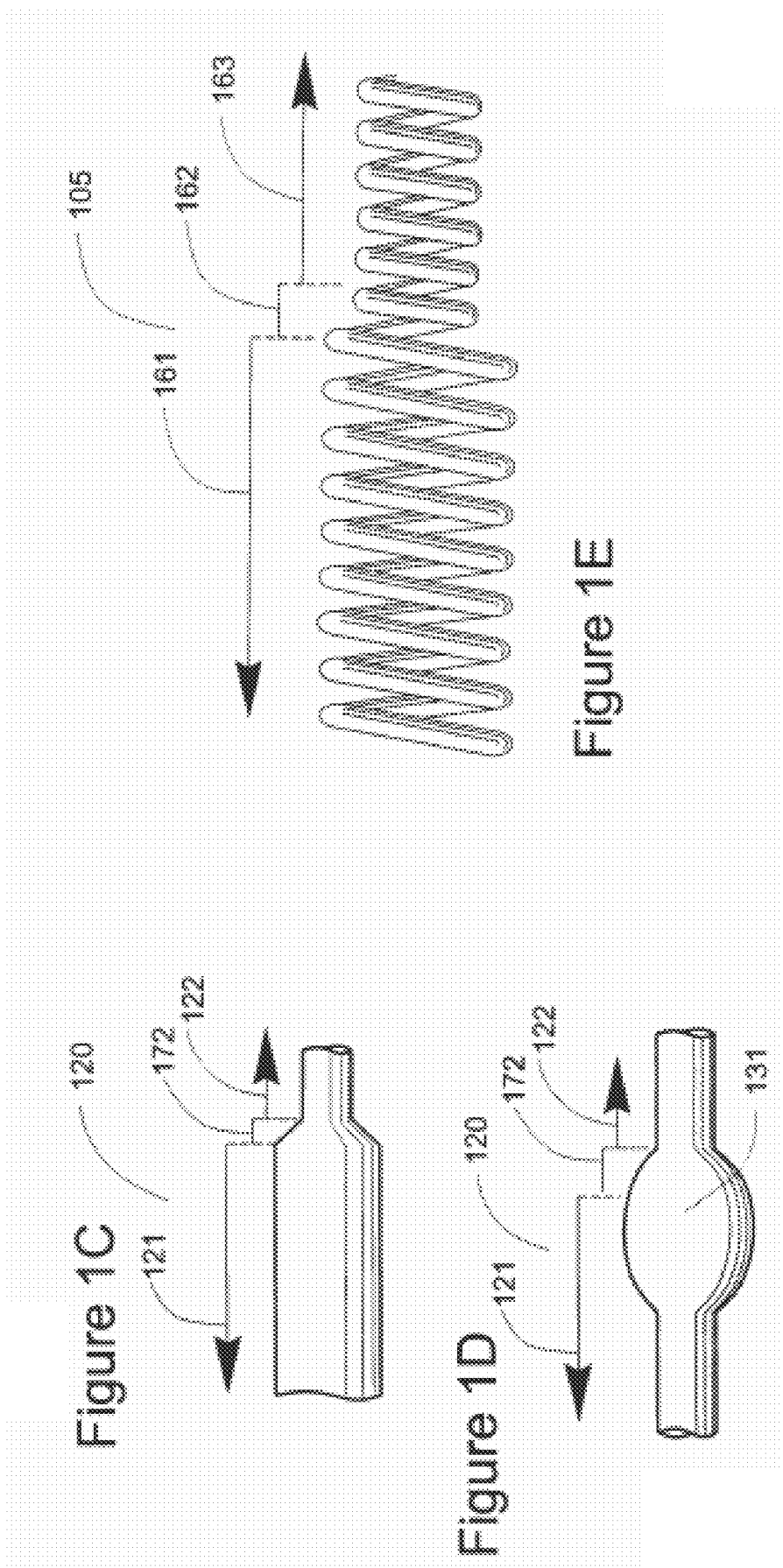

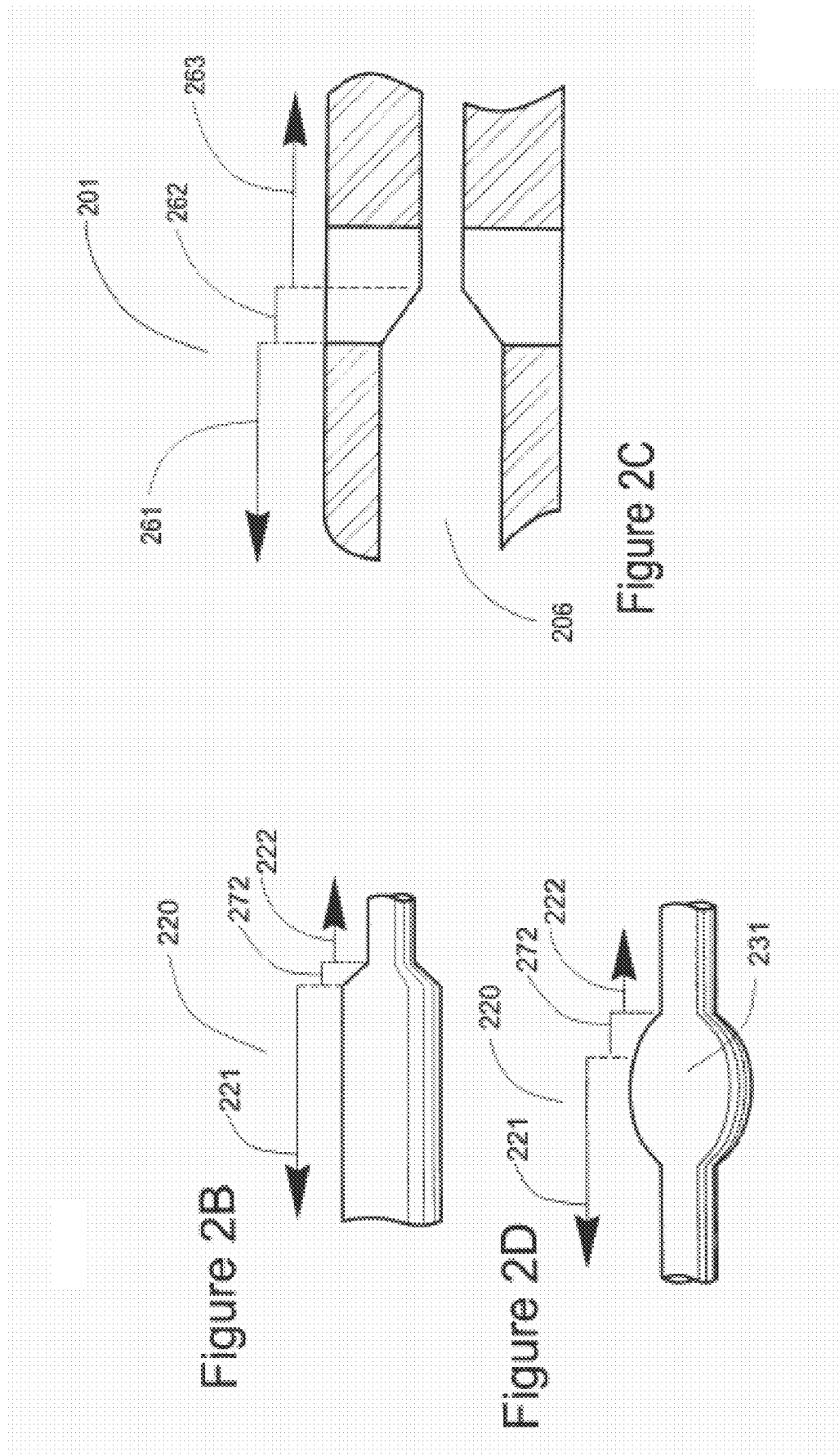

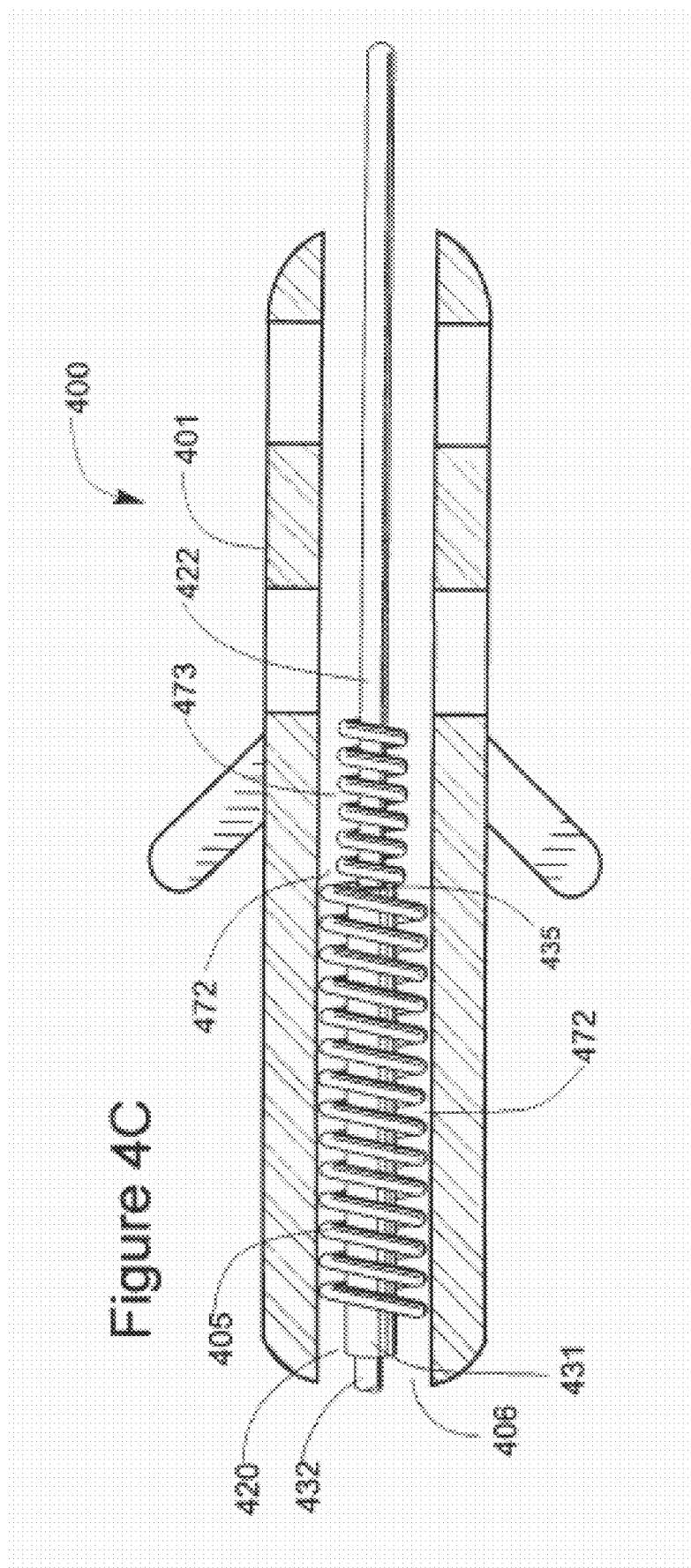

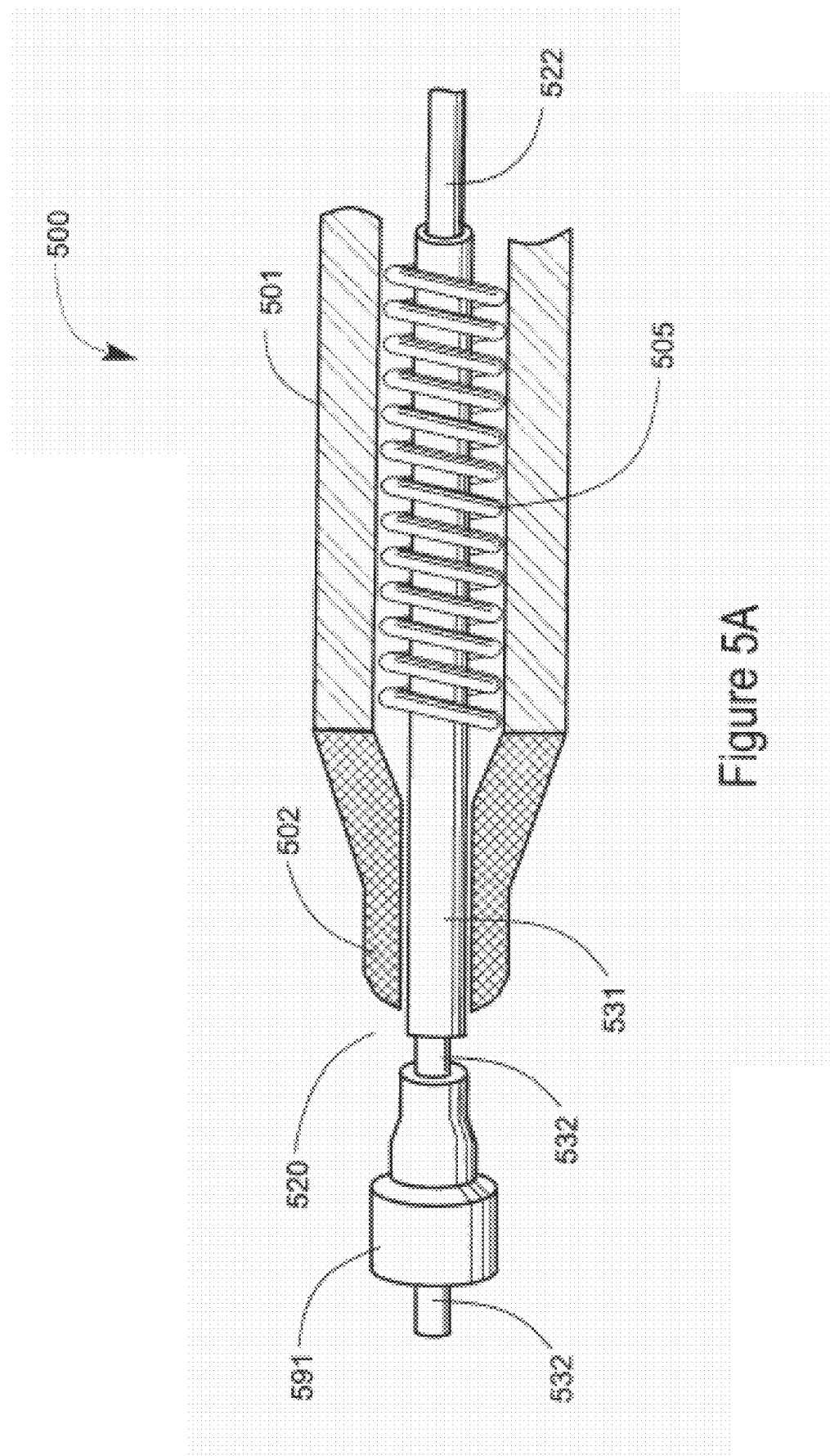

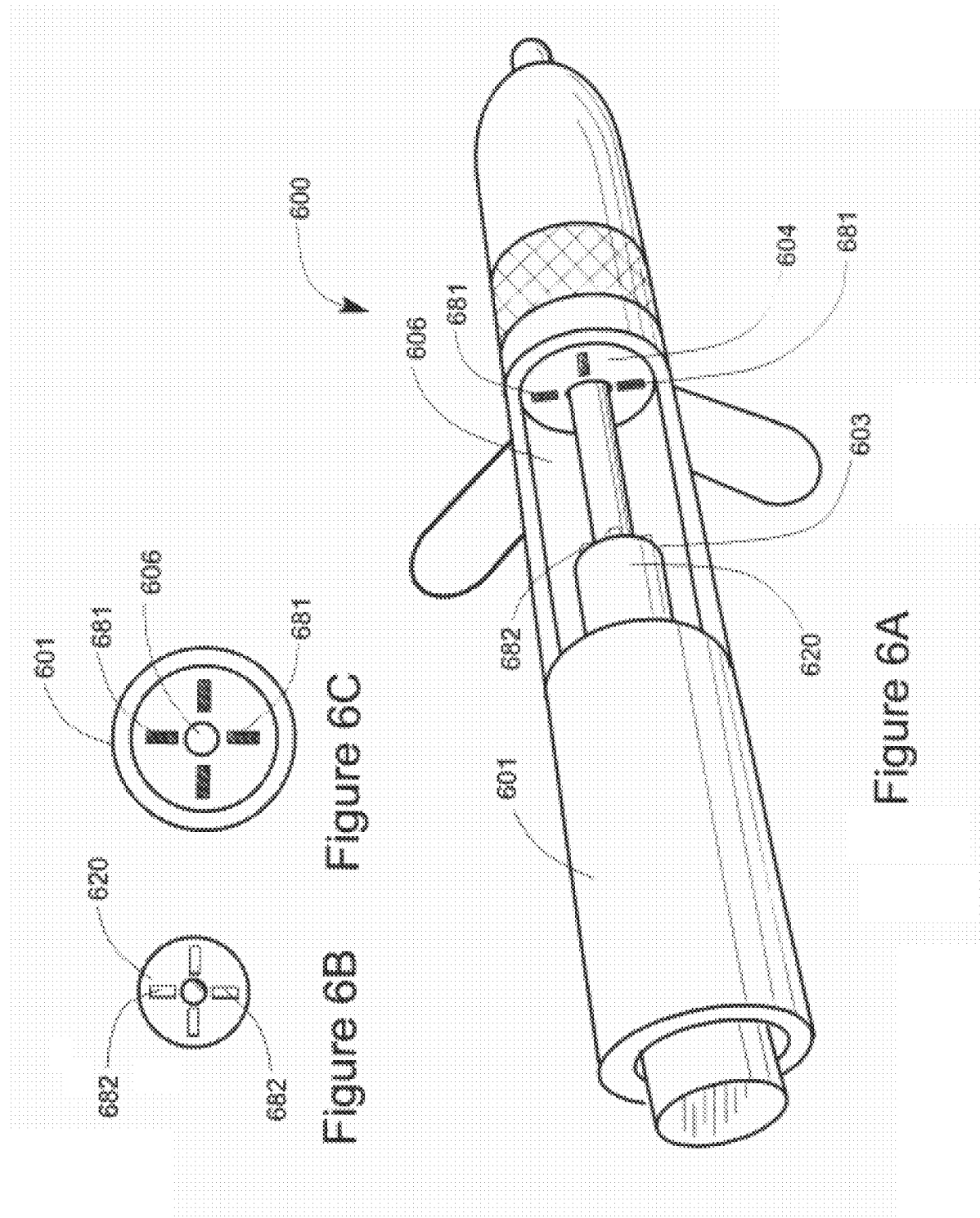

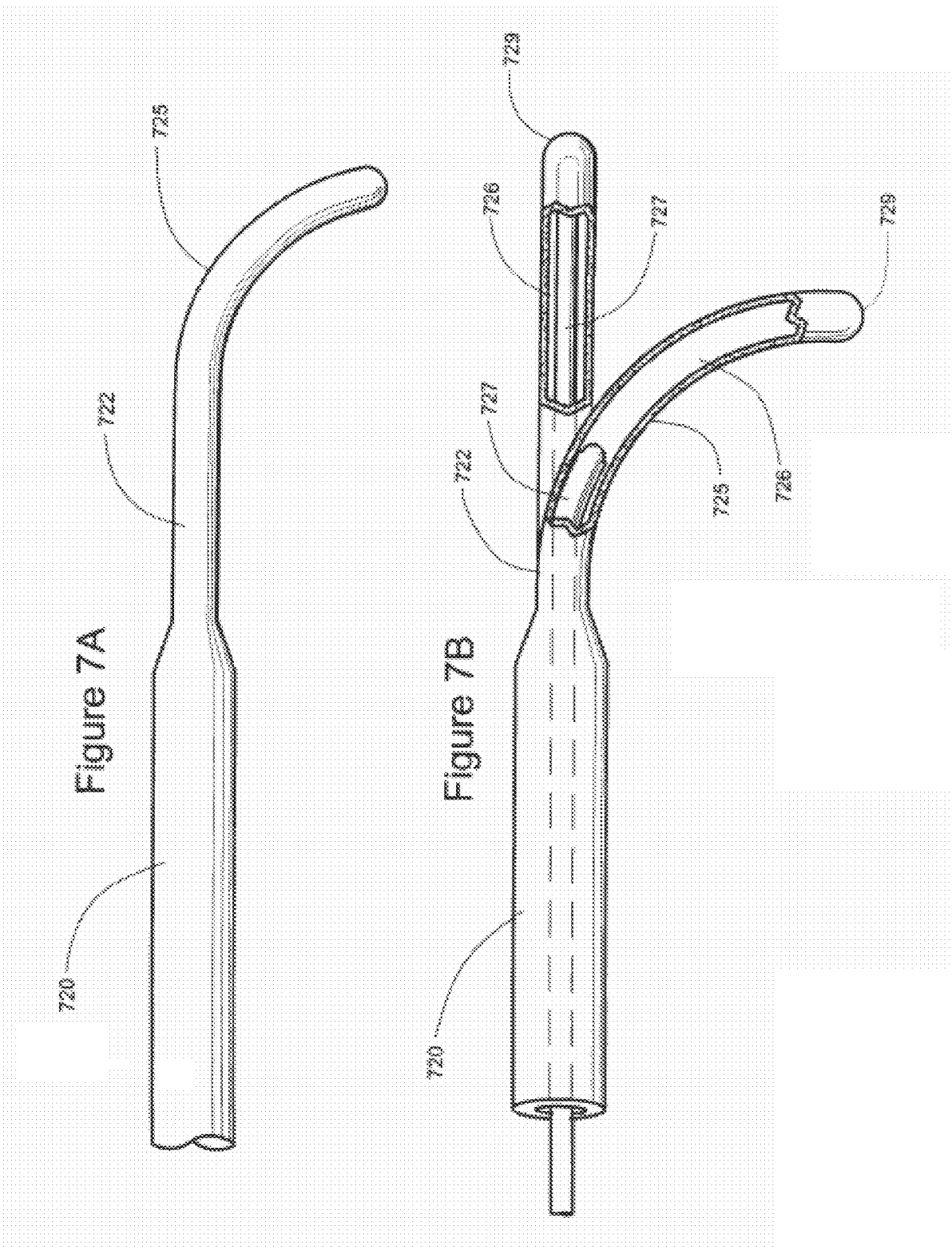

GUIDE WIRE STYLET

RELATED PATENT DOCUMENTS

This application is a division of U.S. patent application Ser. No. 11/432,950 filed on May 12, 2006 which is a division of Ser. No. 10/675,932 filed on Sep. 30, 2003, now U.S. Pat. No. 7,174,222, issued on Feb. 6, 2007, which are incorporated herein by reference in their entireties.

FIELD OF THE INVENTION

The invention relates generally to implantable devices, and, in particular, to methods for facilitating implanting of such devices in the anatomy.

BACKGROUND OF THE INVENTION

Modern medical technology has produced a wide range of body implantable devices. These devices can be used for low risk treatment and diagnosis of a wide range of medical conditions. Implantable cardioverter/defibrillators (ICDs), pacemakers, and cardiac resynchronizers are well-known and effective devices for treating patients with cardiac rhythmic dysfunction. A typical ICD or pacemaker includes a pulse generator and an electrical lead with an electrode at the tip. The ICD/pacemaker implantation procedure generally takes about two hours and is relatively low risk, as it rarely requires open-heart surgery. Usually, one or more lead wires are placed through a large vein in the chest and threaded down to the heart. The lead wires are then connected to the pulse generator, which is placed in a pocket under the skin of the patient.

It may be desirable to position lead electrodes to sense and/or stimulate the left side heart chambers, i.e., the left atrium or the left ventricle. Electrophysiological access to the left ventricle is important, for example, when the patient requires cardiac resynchronization therapy involving pacing the left and right ventricles in accordance with an appropriate timing sequence.

The details of the implantation procedure for a left ventricular access cardiac lead vary depending on the technique used and the patient's condition. In one example, a guiding catheter is introduced through a major blood vessel such as the cephalic vein. The catheter is then moved through the vasculature to locate an access vessel of interest in the heart, such as the coronary sinus ostium. The catheter can be used alone or in combination with a guide wire. After the coronary sinus ostium has been located by the guiding catheter, the cardiac lead may be inserted through the catheter and over the guide wire through the coronary ostium and into coronary sinus or one of its branches.

After the device is successfully implanted, the guide catheter, if used, must be removed from the patient. This removal operation creates a risk of dislodging the cardiac lead because of the forces applied by the retracting catheter against the lead. Dislodging the lead would be problematic, requiring additional time to reseat the lead. Any such time added to the procedure would be needlessly traumatic to the patient.

There is a need for a method and apparatus for maneuvering a lead into position. There is a further need for a method and apparatus for securing a newly implanted lead device while a guiding apparatus is removed, thereby reducing procedure time and patient trauma. The present invention fulfills these and other needs, and addresses other deficiencies of prior art implementations and techniques.

SUMMARY OF THE INVENTION

The present disclosure describes a system and method for inserting a cardiac lead into a patient's anatomy. In one embodiment of the invention, a cardiac lead system includes a cardiac lead having an electrical conductor, a lumen, and a first stop feature. The cardiac lead system further includes a guide member displaceable within the lumen of the cardiac lead. The guide member comprises an elongated body, including a second stop feature, and a guide wire extension. The guide wire extension extends distal to the elongated body of the guide member and is dimensioned to pass through an external distal opening of the lumen. Engagement of the first stop feature of the cardiac lead and the second stop of the guide member prevents further advancement of the elongated body through the cardiac lead lumen.

In another embodiment of the invention, a cardiac lead system includes a cardiac lead including an electrical conductor and a lumen. The cardiac lead lumen comprises a first portion and a second portion, the second portion having a smaller inner diameter relative to the first portion of the cardiac lead lumen. The cardiac lead lumen further comprises a transition region between the smaller diameter portion of the cardiac lead lumen and the larger diameter portion of the cardiac lead lumen.

The cardiac lead system also includes an elongated body and a guide wire extension fixed to a distal end of the elongated body. The guide wire extension has an outer diameter smaller than the outer diameter of the elongated body. The guide member includes a transition region between the elongated body and the guide wire extension. The guide wire extension is dimensioned to allow the guide wire extension to pass into the second portion of the cardiac lead lumen and to pass through an external distal opening of the cardiac lead lumen. Engagement of the transition region of the cardiac lead lumen and the transition region of the guide member prevents further advancement of the guide member through the lumen.

In a further embodiment of the invention, a cardiac lead system includes a cardiac lead having an electrical conductor and a lumen. The lumen comprises a first portion and a second portion distal the first portion. The second portion of the cardiac lead lumen has an inner diameter smaller than the first portion. The cardiac lead lumen also comprises a transition region between the first and second portions of the cardiac lead lumen.

Another embodiment of the invention a cardiac lead system involves a cardiac lead having an electrical conductor and a lumen. The cardiac lead system also includes a guide member displaceable within the cardiac lead lumen. A distal portion of the guide member is dimensioned to pass through an external distal opening of the cardiac lead lumen. The cardiac lead system further includes a stop mechanism. Activation of the stop mechanism prevents further advancement of the guide member through the cardiac lead lumen.

In yet another embodiment of the invention, a cardiac lead system includes a cardiac lead having an electrical conductor and a lumen. The cardiac lead system also includes a guide member displaceable within the cardiac lead lumen. The guide member has a distal portion dimensioned to pass through an external distal opening of the cardiac lead lumen. The cardiac lead system further comprises an inflation member. Activation of the inflation member prevents further advancement of the guide member through the cardiac lead lumen.

In accordance with another embodiment of the invention, a method of advancing an cardiac lead into a destination vessel includes providing a cardiac lead having a lumen and an electrical conductor. A guide member is also provided, the guide member displaceable within the cardiac lead lumen. The method involves moving the guide member within the lumen of a cardiac lead so that a distal portion of the guide member extends beyond a distal external opening in the cardiac lead lumen. A first stop feature of the cardiac lead is engaged by a second stop feature of the guide member to provide a push point. The cardiac lead is advanced into the destination vessel using force applied to the push point.

A further embodiment of the invention involves a method of advancing a cardiac lead into a destination vessel. The method involves providing a cardiac lead and a guide member. The cardiac lead has a lumen and an electrical conductor. The guide member is displaceable within the cardiac lead lumen. The method involves moving the guide member within the cardiac lead lumen so that a distal portion of the guide member extends beyond a distal external opening in the cardiac lead lumen. Activation of a stop mechanism prevents further advancement of the guide member through the cardiac lead lumen. The cardiac lead and the guide member are advanced together into the destination vessel.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIGS. 1A-1E are side views illustrating a cardiac lead system including a multi-diameter coiled conductor and a multi-diameter guide member according to embodiments of the present invention;

FIGS. 2A-2D are side views illustrating a cardiac lead system including a multi-diameter cardiac lead lumen and a multi-diameter guide member of the distal end of the cardiac lead system comprising a guide member according to embodiments of the present invention;

FIGS. 4A-4C are side views of a cardiac lead system comprising a guide member including a sheath and a guide wire displaceable within the sheath according to embodiments of the present invention;

FIG. 5A is a side view of a guide wire clamp that may be used to fix the length of a guide wire extension according to embodiments of the invention;

FIG. 6A illustrates a locking mechanism that may be used to lock the guide member and the cardiac lead to allow concurrent rotation of the cardiac lead and the guide member so that the guide member and the cardiac lead may be torqued together to advance the cardiac lead system according to embodiments of the invention;

FIGS. 6B and 6C illustrate cross sections of the guide member and the cardiac lead locking elements, respectively, according to embodiments of the invention;

FIG. 7A is a side view of a guide member having a preformed shape; and

FIG. 7B is a cut away view of a deflectable guide member using a moveable core according to embodiments of the invention.

Figure 1B:
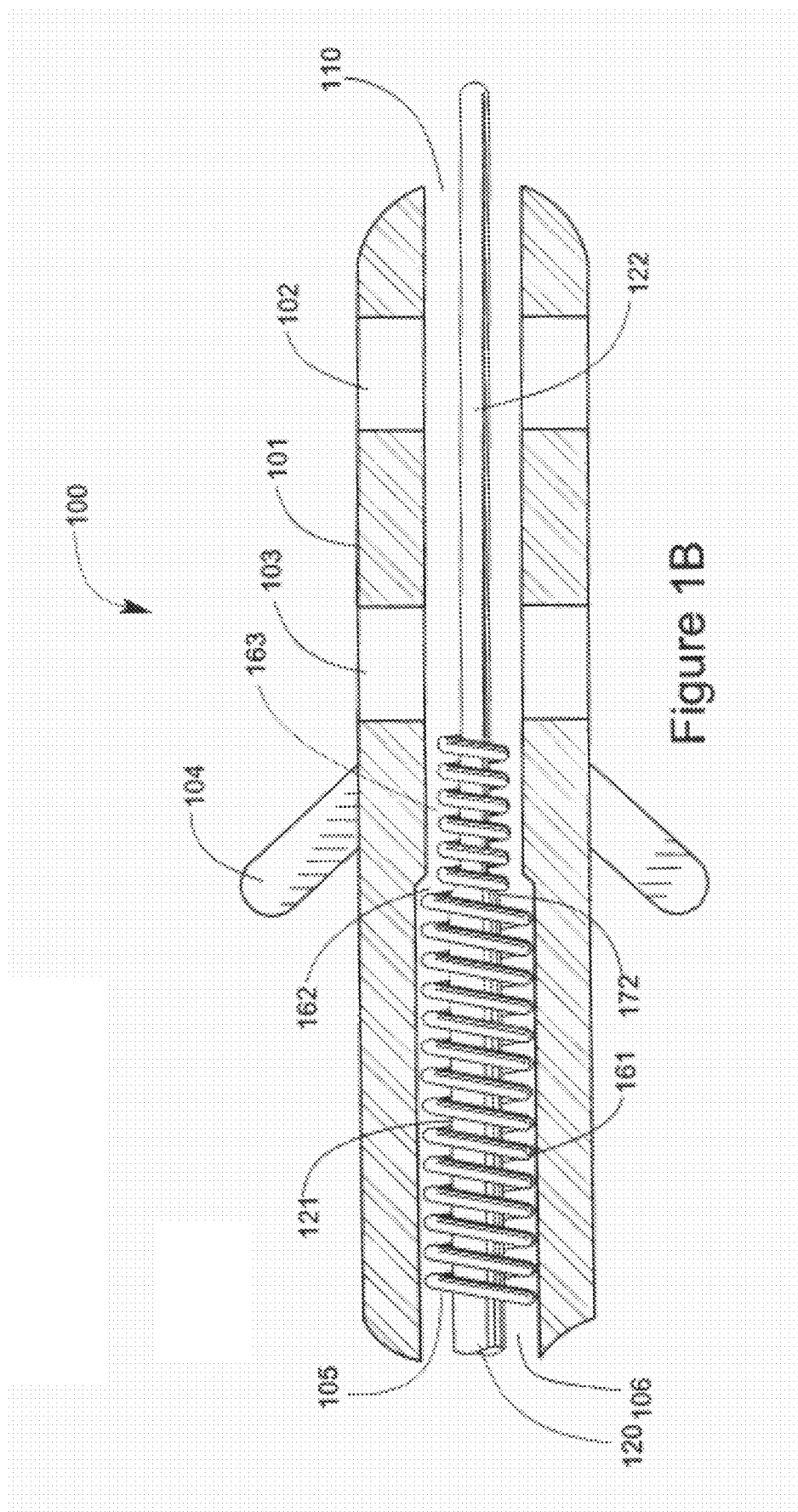
Figure 2A:
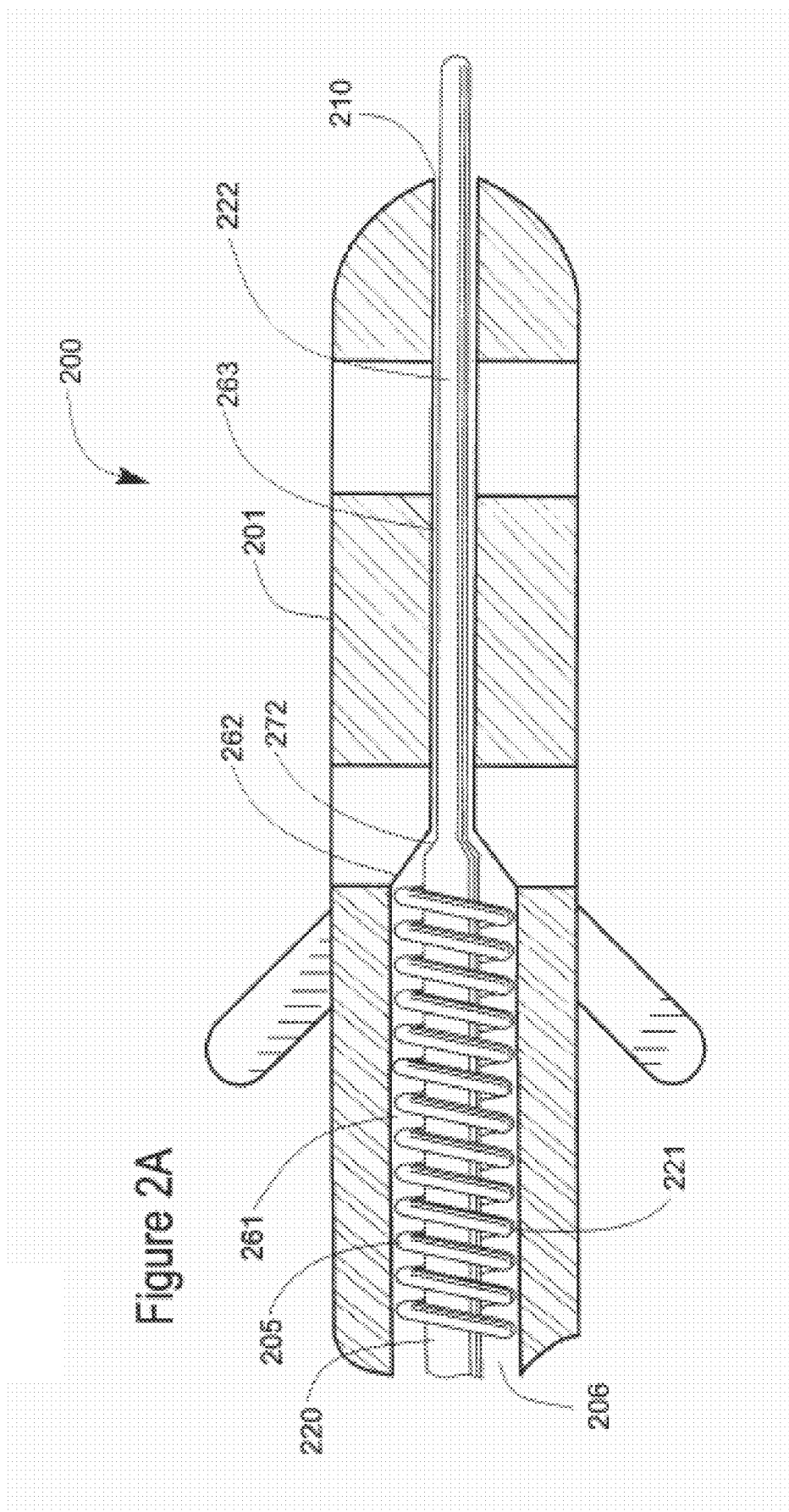

While the invention is amenable to various modifications and alternative forms, specifics thereof have been shown by way of example in the drawings and will be described in detail herein. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

The present disclosure describes cardiac lead systems and methods involving implantation of a cardiac lead or other similar device into a patient's vasculature. Various embodiments of the invention have been found to be particularly useful in connection with implantation of cardiac leads to electrically access a patient's left ventricle, for example, through the coronary sinus vein.

According to various embodiments, the cardiac lead system of the present invention includes a cardiac lead having an open or openable lumen and a guide member that is displaceable within the lumen. The cardiac lead includes an external distal opening in communication with the lumen. The external distal opening may be covered by an openable flap or a seal, for example. In some embodiments, the cardiac lead system comprises a stop mechanism or stop features including, for example, a first stop feature on the cardiac lead that is engagable by a second stop feature positioned on an elongated body of the guide member. When activated or engaged, the stop mechanism or stop features prevent further advancement of the elongated body of the guide member through the cardiac lead.

The guide member also includes a guide wire extension positioned distal to the elongated body. The guide wire extension is dimensioned to extend through the exterior opening of lumen at the distal end of the cardiac lead. The cardiac lead may include a first stop feature located, for example, near the distal end of the cardiac lead. A second stop feature may be positioned on the elongated body, for example, between the elongated body and the guide wire extension. Engagement of the first stop feature of the cardiac lead and the second stop feature of the guide member prevents further advancement of the elongated body through the lumen. Engagement of the first and second stop features provides a push point to advance the lead forward through the patient's vasculature.

The guide wire extension is dimensioned so that if the first and the second stop features are engaged, the guide wire extension extends or is extendable beyond the distal opening of the cardiac lead. The guide wire extension may have a pre-formed shape, or may be deflectable to aid in directing the cardiac lead to a desired location. The cardiac lead system described herein may be used to position a wide variety of cardiac leads, including cardiac pacing and/or defibrillation leads, used to sense physiological activity and/or provide electrical stimulation.

Referring now to the drawings, FIGS. 1A and 1B show cross sectional views the distal portion of a cardiac lead system 100 that may be used to guide a cardiac lead 101 into a desired location of the patient's vasculature in accordance with an embodiment of the invention. FIG. 1C illustrates portions of a first configuration of a guide member 120 having a single diameter elongated body 121 and a guide wire extension 122. FIG. 1D illustrates portions of a second configuration of a guide member 120, having a multi-diameter elongated body 121, including an enlarged portion 131. The guide member 120 also includes a guide wire extension 122. FIG. 1E illustrates portions of a multi-diameter coiled conductor 105.

As illustrated in FIGS. 1A-1E, the cardiac lead system 100 includes a cardiac lead 101 having at least one lumen 106 with an external opening 110 at the distal tip of the cardiac lead 101. The external opening 110 may be covered by an openable flap, seal, or other device. The cardiac lead 101 includes one or more electrodes 103 and may optionally include a steroid collar 102 for drug delivery. The embodiment illustrated in FIG. 1A shows one steroid collar 102 positioned distal to the electrode 103 with a space between the steroid collar 102 and the electrode 103. Other configurations are also possible involving any number of steroid collars 102 and any number of electrodes 103. For example, the steroid collar 102 and may be immediately adjacent the electrode 103. In another example, one or more steroid collars 102 may be positioned proximal to the electrode 103. In a further example, one or more steroid collars 103 may be positioned on either side of the electrode 103. The electrode 103 may be at the tip of the lead 101 or along the body of the lead. Other configurations are possible and are considered to be within the scope of the invention. The cardiac lead 101 may also optionally include a fixation device, such as one or more tines 104, or other surface projections, or a pre-formed shape, for stabilizing the lead within the patient's vasculature.

In the embodiments illustrated by FIGS. 1A-1E, the cardiac lead 101 includes a multi-diameter coiled conductor 105 positioned within the lumen 106 of the cardiac lead 101. The coiled conductor 105 includes a first portion 161, associated with a first inner diameter, a second portion 163, associated with a smaller inner diameter than the first portion, and a transition region 162. The first portion 161 of the coiled conductor 105 extends along most of the length of the cardiac lead 101. The inner diameter of the coiled conductor 105 narrows to a smaller inner diameter at a transition region 162 near the distal tip of the cardiac lead 101. For example, the coiled conductor 105 may narrow to a smaller inner diameter about 1 cm, or other distance, from the distal tip of the cardiac lead 101.

At the transition region 162 of the coiled conductor, the diameter of the lumen formed by the coiled conductor 105 is decreased. The decease in the diameter of the lumen formed by the coiled conductor 105 may be accomplished by an abrupt or tapered transition region 162. In one example, the first portion 161 of the coiled conductor may have an inner diameter of about 0.025". The coiled conductor 105 may abruptly narrow at a transition region 162 to a second portion 163 having an inner diameter of about 0.018". Other dimensions for the inner diameters of the first and second portions 161, 163 of the coiled conductor 105 are also possible so long as the inner diameter of the first portion 161 is larger relative to the inner diameter of the second portion 163.

The guide member 120 includes an elongated body 121 having an outer diameter dimensioned to be displaceable within the lumen formed by the first portion 161 of the multi-diameter coiled conductor 105. The guide member 120 also includes a guide wire extension 122 extending distally beyond the elongated body 121. In the configurations illustrated in FIGS. 1A-1E, the guide wire extension 122 has an outer diameter dimensioned to be displaceable within the lumen formed by the second portion 163 of the multi-diameter coiled conductor 105 and to extend through the exterior opening 110 of the cardiac lead lumen 106 beyond the distal tip of the cardiac lead 101.

In one configuration, illustrated in FIG. 1C, the elongated body 121 has a single outer diameter, for example, an outer diameter of about 0.020 inches. The guide wire extension 122 has an outer diameter, for example, of about 0.014 inches.

In another configuration, illustrated in FIG. 1D, the multi-diameter elongated body 121 has an enlarged portion 131. In this configuration, the guide wire extension 122 and the portion of the elongated body 121, excluding the enlarged portion 131, may have an outer diameter, for example, of about 0.014 inches. The enlarged portion 131 of the elongated body may have an outer diameter, for example, of about 0.020 inches.

Other dimensions for the elongated body 121 and/or the guide wire extension 122 are also possible so long as the largest outer diameter of the elongated body 121 allows displacement of the elongated body 121 through the lumen formed by the first portion 161 of the coiled electrode and the outer diameter of the guide wire extension 122 allows displacement of the guide wire extension 122 through the lumen formed by the second portion 163 of the coiled conductor 105. In this illustrative embodiment, the guide member 120, including the elongated body 121 and the guide wire extension 122, and the coiled conductor 105 are dimensioned to permit the guide wire extension 122 to extend through the smaller diameter portion 163 of the coiled conductor 105 while restricting movement of the elongated body 121 through the smaller diameter portion 163 of the coiled conductor 105.

The elongated body 121 and the guide wire extension 122 may be formed by various methods. For example, the elongated body 121 and the guide wire extension 122 may be formed as separate sections with all or portions of the elongated body 121 assembled over and secured to the guide wire extension 122. Alternatively, the elongated body 121 and the guide wire extension 122 may be formed as a single piece. All or portions of a proximal region, comprising the elongated body 121, may be formed to have a larger diameter than a distal region, comprising the guide wire extension 122.

A transition region 172 between the elongated body 121 and the guide wire extension 122 may provide an abrupt or tapered transition between the larger outer diameter of the elongated body 121 and the smaller outer diameter of the guide wire extension 122 located at the distal end of the guide member 120. The guide member transition region 172 may be formed by a variety of techniques, and may comprise a polymer molding, solder ball, or a metallic material ground to a smooth contour. The elongated body 121 and/or the guide wire extension 122 may be formed from a metallic material such as stainless steel (304V), nitinol (NiTi), or a polymeric or composite material. The length of the guide wire extension 122 may vary depending on the application and the patient's anatomy. The guide wire extension 122 may have a length in a range, for example, from about 5 mm to about 30 mm, or other length.

In the embodiments illustrated in FIGS. 1A through 1E, the coiled conductor transition region 162 and the guide member transition region 172 form first and second stop features, respectively. As illustrated in FIG. 1A, the guide member 121 may be displaced through the larger diameter section 161 of the coiled conductor 105. Engagement of the guide member transition region 172, forming the first stop feature, with the coiled conductor transition region 162, forming the second stop feature, prevents further forward motion of the elongated body 120 through the lumen 106.

FIG. 1B illustrates the guide member 120 in a fully deployed orientation within the cardiac lead 101. Engagement of the transition region 162 of the coiled conductor 105 and the transition region 172 of the guide member 120 prevents further advancement of the guide member 120 through the lead 101. The guide wire extension 122 extends through the smaller diameter portion 163 of the coiled conductor 105 and through the external opening 110 at the distal tip of the cardiac lead 101.

FIGS. 2A-2D illustrate further embodiments of the cardiac lead system 200. In one configuration, the cardiac lead 201 includes a multi-diameter inner lumen 206 with an external opening 210 at the distal tip of the cardiac lead 201. The external opening 210 may be covered by an openable flap, seal, or other openable component. The lumen 206 of the cardiac lead 201 comprises a first portion 261 having a first diameter throughout a majority of the cardiac lead 201. A predetermined distance from the distal end of the cardiac lead 201, the diameter of the lumen 206 narrows to a form a smaller diameter portion 263 of the lumen. A transition region 262 between the larger 261 and smaller 263 diameter portions of the lumen 206 may be abrupt or tapered. The transition region 262 between the first portion 261 of the lumen having a larger diameter and the second portion 263 of the lumen having a smaller diameter forms a first stop feature.

As illustrated in FIGS. 2A-2D, a single diameter coiled conductor 205 may be positioned within the larger diameter portion 261 of the cardiac lead lumen 206. The coils of the coiled conductor 205 form a lumen through which a guide member 220 having the configuration previously described in connection with FIGS. 1A-1D is deployed. The guide member 220 includes an elongated body 221 and a guide wire extension 222. The elongated body 221 of the guide member 220 is displaceable within the lumen formed by the coils of the coiled conductor 205 positioned within the larger diameter portion 261 of the cardiac lead lumen 206. The outer diameter of the elongated body 221 is dimensioned to prevent displacement within the smaller inner diameter portion 263 of the cardiac lead lumen 206.

As previously described, a guide wire extension 222 is located distal to the elongated body 221. The transition region 272 of the guide member 220 forms a second stop feature. The outer diameter of the guide wire extension 222 is selected to allow the guide wire extension 222 to pass through the smaller diameter portion 263 of the cardiac lead lumen 206 and out of the external opening 210 at the distal tip of the cardiac lead 201. Engagement of the first stop feature, formed by the transition region 262 of the lumen, and the second stop feature, formed by the transition region 272 of the guide member 220, prevents further advancement of the guide member 220 through the cardiac lead 201 and provides a push point for moving the cardiac lead 201 through the patient's vasculature.

Although the examples shown in FIGS. 1A-1E and FIGS. 2A-2D show tapered transition regions of the coiled conductor or the lead lumen that engage a transition region of the guide member, other physical structures may be utilized to form the first and second stop features. The stop features may be formed by any structure or combination of structures that restricts advancement of the elongated body while allowing the guide wire extension to be moved within a distal portion of the cardiac lead lumen and through the external opening of the cardiac lead.

Figure 3:
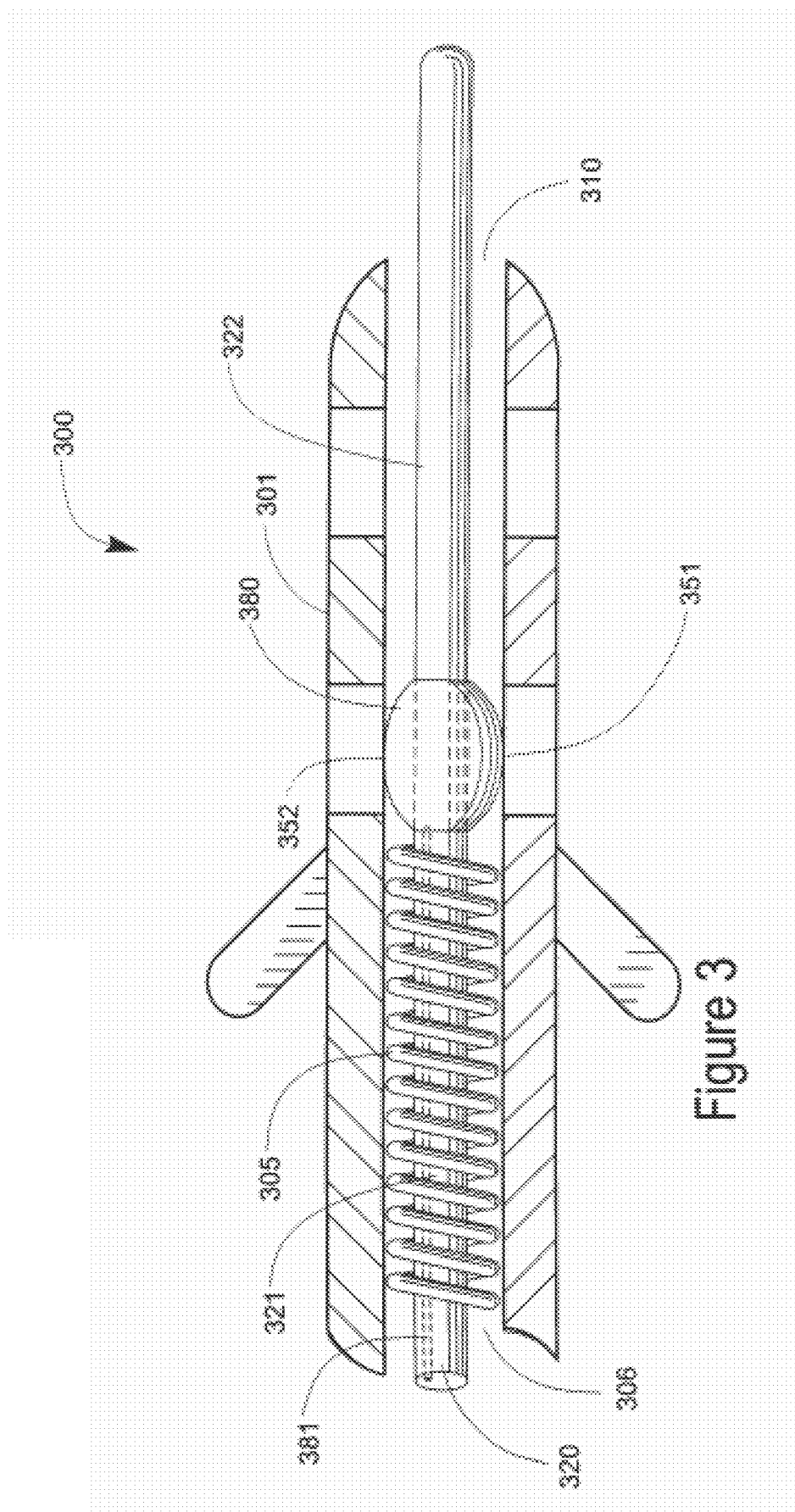
FIG. 3 is a side view of cardiac lead system comprising an inflation element according to embodiments of the present invention.

In another embodiment, the guide member incorporates a stopping mechanism for stopping the advancement of the guide member and/or locking the guide member to the cardiac lead anywhere along the length of the lead, or along the entire length of the lead. FIG. 3 is a cross sectional view of an implementation of a cardiac lead system 300 according to this approach. A single diameter coiled conductor 305 is positioned within a single diameter lumen 306 of the cardiac lead 301. The guide member 320 comprises an elongated body 321 including a one or more inflation members 380, e.g., an inflatable rigid balloon, positioned at one or more appropriate locations along the elongated body 321. In this configuration, the guide member 320 may comprise a hypo tube, a hollow metal tube similar to a hypodermic needle.

The inflation member 380 forms a stop mechanism that, when activated, prevents further advancement of the guide member 320 through the lumen 306. The inflation member 380 is in communication with an inflation lumen 381 in the guide member 320 to facilitate inflation and deflation of the inflation member 380 from the proximal end of the guide member 320. The portion of the guide member 320 distal the inflation member 380 forms a guide wire extension 322 that is extendable through the external opening 310 of the cardiac lead lumen 306.

In this configuration, the inner surface 351 of the cardiac lead lumen 306 defines a first stop feature. The contact point 352 of the inflated inflation member 380 with the inner surface 351 of the cardiac lead lumen 306 defines a second stop feature. When inflated, the contact point 352 of the outer surface of the balloon 380 engages the inner surface 351 of the cardiac lead lumen 306, preventing further advancement of the guide member 320 through the cardiac lead lumen 306. Using this approach, the guide member 320 may be locked to the cardiac lead 301 anywhere along the length of the lead 301. With the guide member 320 and the cardiac lead 301 locked together, the cardiac lead system 300 may be advanced or torqued together. As illustrated in FIG. 3, the inflation balloon 380 may be inflated inside the lumen 306, but beyond the conductor coil 305.

In another example, the inflation balloon 380 may be inflated inside the conductor coil 305, locking the guide member 320 to the cardiac lead 301. In this example, upon inflation, the outer surface 351 of the inflation balloon 380 engages the inner surface of the conductor coil 305. In this configuration, the guide member 320 may be locked to the cardiac lead 301 anywhere along the length of the cardiac lead 301. The length of the balloon 380 is variable and can lock onto the cardiac lead 301 at a specific point or over an extended length.

The ability to push the cardiac lead system 300 through the patient's vasculature using the guide member 320 facilitates placement of the lead 301 into a desired location. The guide wire extension 322, positioned distal the inflation balloon 380 is extendable through cardiac lead lumen 306 and out of the external opening 310 at the distal tip of the cardiac lead 301. The guide wire extension 322 may be straight, have a preformed curve, or may be deflectable to guide the insertion and movement of the cardiac lead system 300, as described in more detail below.

Figure 4A:
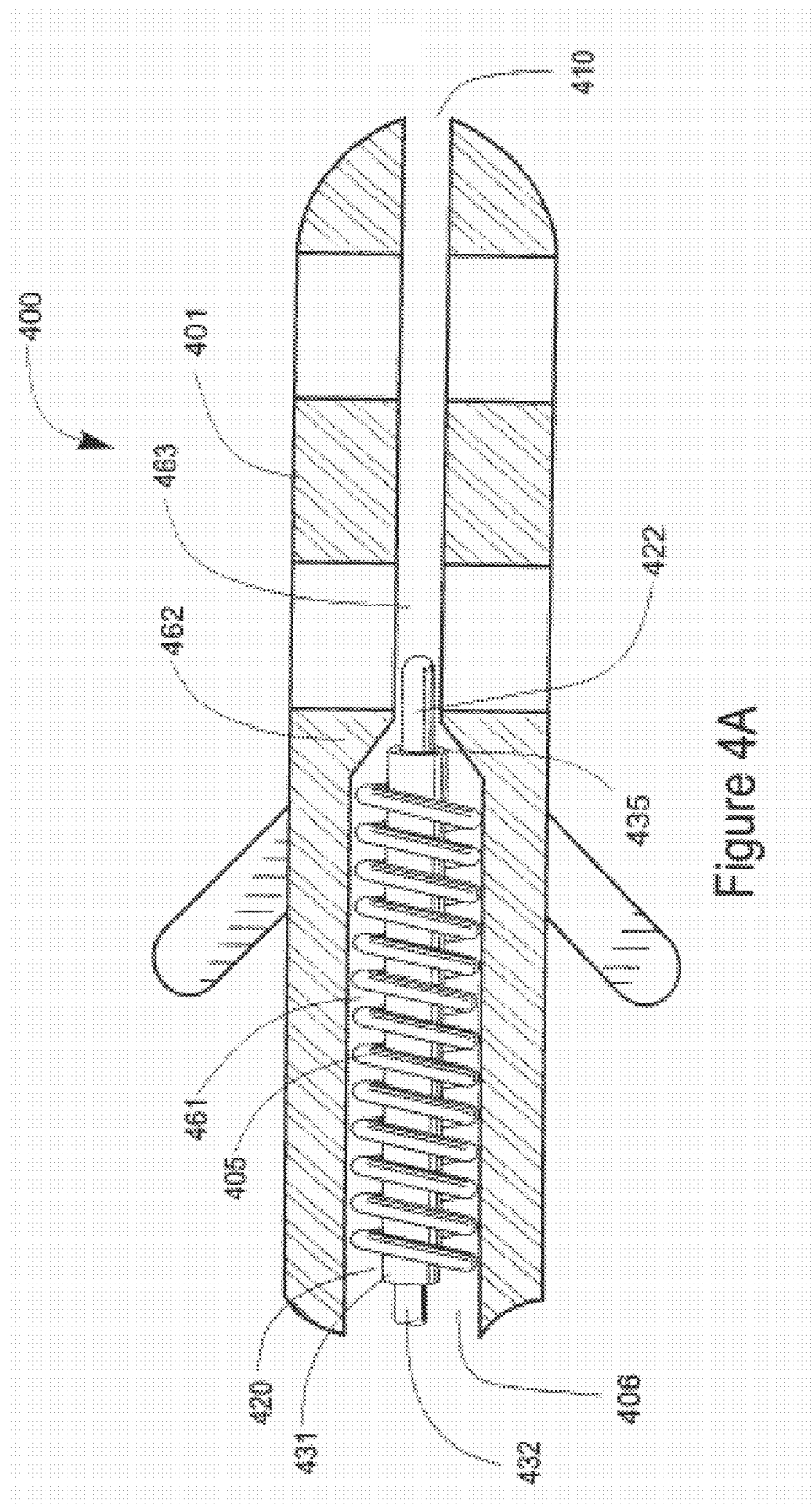
Figure 4B:
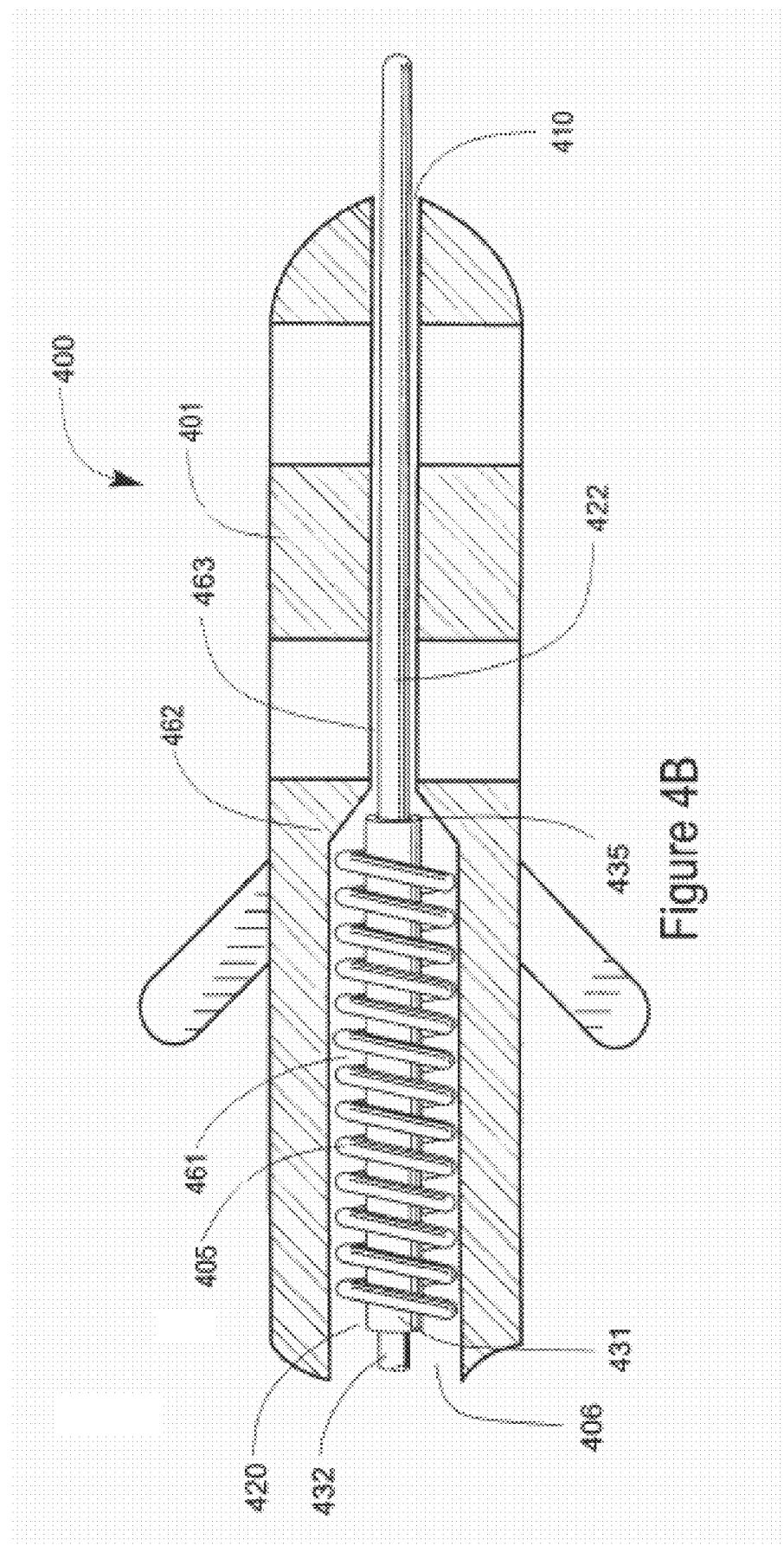

FIGS. 4A and 4B illustrate cross sectional views of yet another embodiment of the cardiac lead system 400. In this embodiment, the cardiac lead system 400 includes cardiac lead 401 having a multi-diameter lumen 406. A guide member 420 comprises a hollow elongated body 431, for example, a sheath or tube. A guide wire 432 is displaceable within the hollow elongated body 431. The hollow elongated body 431 may be formed of, for example, a polymer or a metal hypotube, as previously described. The guide wire 432 may be formed of, for example, a metallic material such as stainless steel (304V), nitinol (NiTi), or a polymeric or composite material. The outer diameter of the guide wire 432 is dimensioned to allow the guide wire 432 to fit within the smaller diameter portion 463 of the cardiac lead lumen 406 and extend through the external opening 410 at the distal end of the cardiac lead 401.

The cardiac lead 401 may include a coiled conductor 405 positioned within the cardiac lead lumen 406. The outer diameter of the hollow elongated body 431 is selected so that the hollow elongated body 431 fits within the lumen formed by the coils of the coiled conductor 405, but prevents insertion of the hollow elongated body 431 into the smaller diameter portion 463 of the cardiac lead lumen. The distal end of the sheath 435 engages the transition region 462 of the cardiac lead lumen 406 preventing further advancement of the hollow elongated body 431 through the lumen 406. The transition region 462 of the cardiac lead lumen forms a first stop feature and the distal end 435 of the hollow elongated body 431 forms the second stop feature. Engagement of the first and second stop features prevent further movement of the hollow elongated body 431 through the cardiac lead lumen 406.

The guide wire 432 is displaceable within the hollow elongated body 431 and is dimensioned to fit within the smaller diameter portion 463 of the cardiac lead lumen 406. By moving the guide wire 432 in relation to the hollow elongated body 431, the portion of the guide wire extending beyond the distal end 435 of the hollow elongated body 431, denoted as the guide wire extension 422, may be adjusted in length. The length of the guide wire extension 422 may be fixed, for example, by a clamping device, shown in FIG. 5, positioned at the proximal end of the cardiac lead system 400. FIG. 4A illustrates the guide wire 432 deployed through the hollow elongated body 431 and into the smaller diameter portion 463 of the cardiac lead lumen. FIG. 4B illustrates the guide member 420 fully deployed within the cardiac lead 401 with the guide wire extension 422 extending beyond the distal opening 410 of the cardiac lead 401.

FIG. 4C illustrates an embodiment of a cardiac lead system 400 comprising a guide member 420 including a hollow elongated body 431 and a guide wire 432 displaceable within the hollow elongated body 431. In this implementation, the cardiac lead 401 incorporates a multi-diameter coiled conductor 405 defining a multi-diameter lumen within the cardiac lead 401 as previously discussed in connection with FIGS. 1A and 1B. The transition region 472 of the multi-diameter coiled conductor 405 forms a first stop feature.

The outer diameter of the hollow elongated body 431 is selected so that the hollow elongated body 431 fits within the larger diameter portion 471 of the coiled conductor 405 but prevents insertion of the hollow elongated body 431 into the smaller diameter portion 473 of the coiled conductor 405. The distal end 435 of the hollow elongated body 431 provides a second stop feature. When the first stop feature, formed by the transition region 472 of the coiled conductor 405, engages the second stop feature, formed by the distal end 435 of the hollow elongated body 431, further movement of the hollow elongated body 431 through the cardiac lead 401 is prevented.

As previously discussed, the guide wire 432 may be moved in relation to the hollow elongated body 431. Moving the guide wire 432 allows adjustment of the length of the portion of the guide wire, denoted the guide wire extension 422, extending beyond the distal end 435 of the hollow elongated body 431. The length of the guide wire extension 422 may be fixed, for example, by a clamping device positioned at the proximal end of the cardiac lead system 400 as illustrated in FIG. 5.

FIG. 5A illustrates a guide wire clamping device 591 positioned at the proximal end of the cardiac lead system 500. In this configuration, the cardiac lead 501 includes a coiled conductor 505 forming an inner lumen. A guide member 520, including a hollow elongated member 531 and a guide wire 532, is displaceable in the cardiac lead 501 through the lumen formed by the coiled conductor 505. The guide member 520 extends through the cardiac lead 501 and out of a proximal opening in the terminal pin 502 of the cardiac lead 501. By moving the guide wire 532 longitudinally in relation to the hollow elongated member 531, the physician can adjust the length of the guide wire extension 522 that extends beyond the distal tip of the cardiac lead 501.

When the appropriate length of the guide wire extension 522 is selected, guide wire clamping device 591 may be activated, preventing further movement of the guide wire extension 522 beyond the hollow elongated body 531. The guide wire clamping device 591 may operate, for example, like a chuck, to clamp the guide wire 532 and prevent further advancement of the guide wire 532 through the hollow elongated member 531. The clamping device may also clamp onto both the guide wire 532 and the hollow elongated member 531, locking the two together.

Figure 5B:
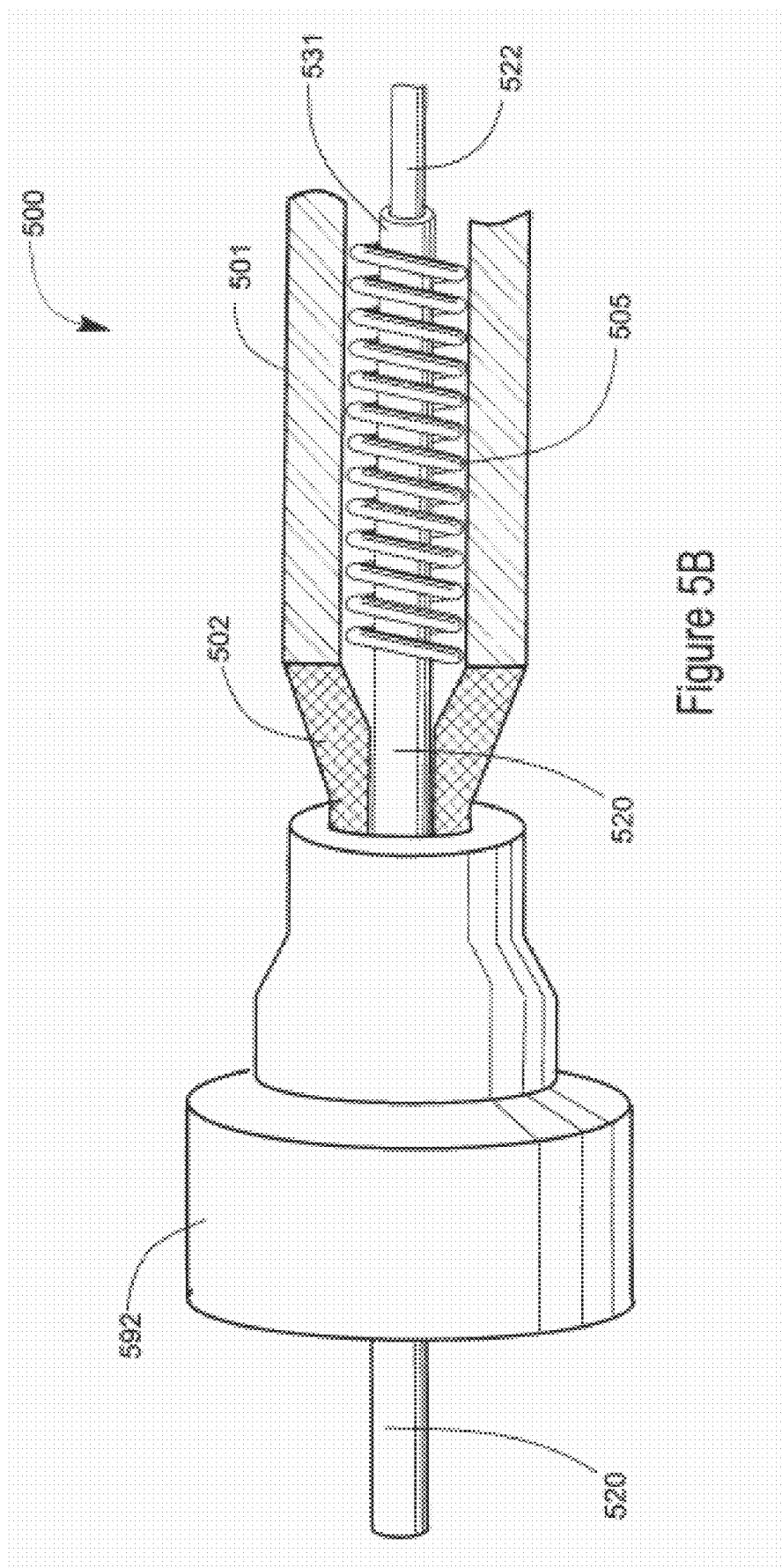
FIG. 5B is a side view of a stop mechanism for attaching a terminal pin of the cardiac lead to the guide member according to embodiments of the invention.

In a further embodiment of the cardiac lead system, there may be no narrowing of the lead, either in the lead or in the conductor coil. A stop mechanism may be provided at the proximal end of the cardiac lead 501, as shown in FIG. 5B. In this embodiment, the stop mechanism 592, which may be implemented as a clamp or a chuck, may clamp onto the guide member 520, onto the guide wire 532, and/or onto a terminal pin 502 of the lead 501, or other feature of the lead 501. Activation of the stop mechanism locks the lead 501 and the guide member 520 together outside the patient. The guide member 520 and the lead 501 may then be advanced together through the patient's vasculature and into the destination vessel. Although the embodiment illustrated in FIG. 5B illustrates the guide member 520 including a hollow elongated member 531 and a guide wire extension 522, a single diameter solid guide member, or a multi-diameter solid guide member as illustrated in FIGS. 1-2 may alternatively be used.

Figure 5C:
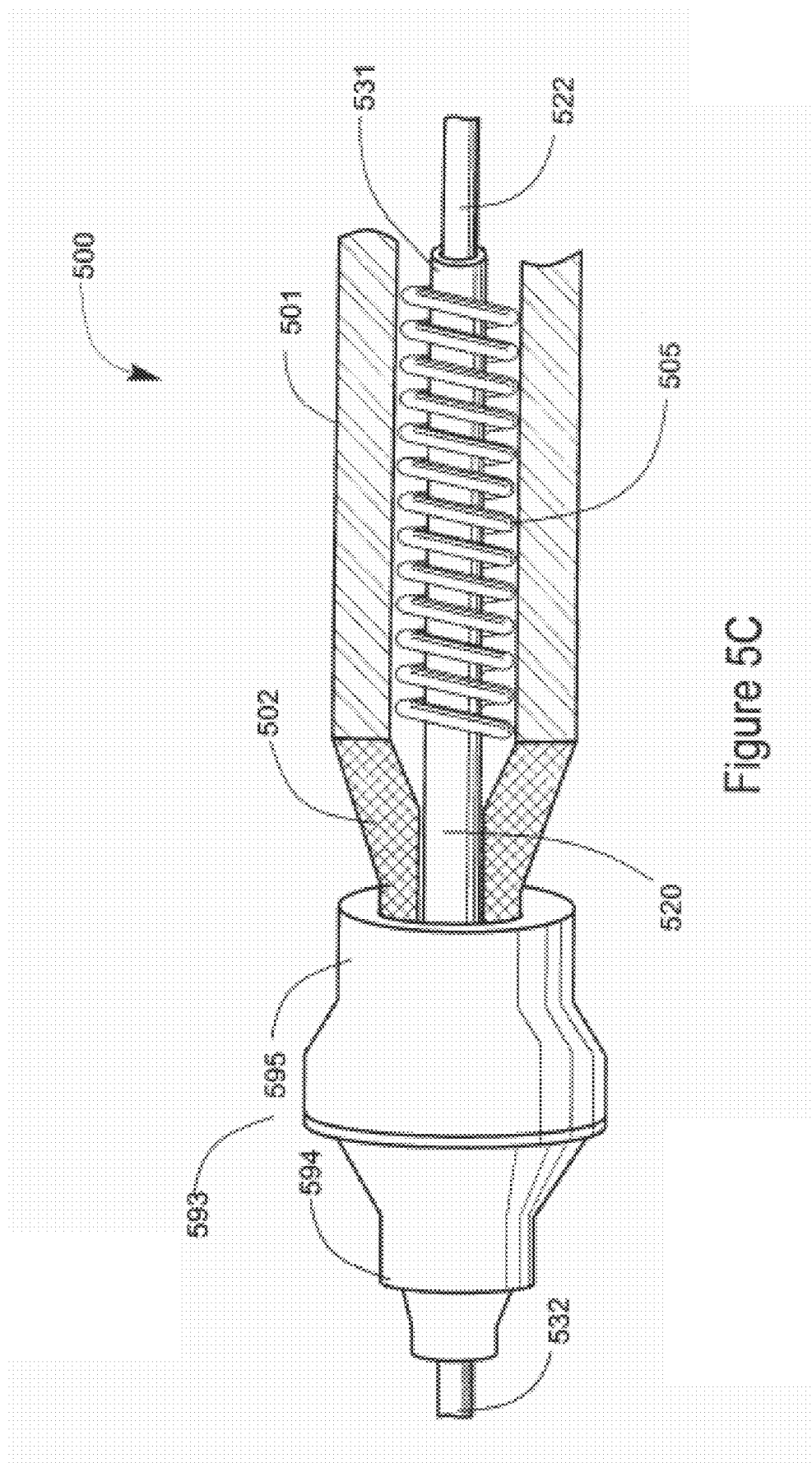
FIG. 5C is a side view of a stop mechanism for attaching the guide member to the guide wire, to the terminal pin of the cardiac lead, or both, according to embodiments of the invention.

In another embodiment, a stop mechanism may be attached to the guide member 520. FIG. 5C illustrates a stop mechanism implemented as a clamp 593 fixed to the hollow elongated member 531 of the guide member 520. The clamp 593 may comprise a double chuck used to clamp the hollow elongated member 531 to the guide wire 532, the cardiac lead 501, or both. Upon activation of a first portion 594 of the clamp 593, the hollow elongated member 531 is locked to the guide wire 532, thus preventing further advancement of the guide wire 532 through the hollow elongated member 531. Upon activation of a second portion 595, the hollow elongated member 531 is locked to the terminal pin 502 or other feature of the lead. The guide member 520 and the lead 501 may then be advanced together through the patient's vasculature and into the destination vessel.

As described above in connection with FIGS. 1-4, the engagement of stop features of the cardiac lead and the guide member provide a push point at the distal end of the cardiac lead for advancing the cardiac lead system through the vasculature. In another embodiment, the cardiac lead system may incorporate one or more mating sections that lock the guide member to the cardiac lead near the distal end of the cardiac lead, or at other locations. Locking the guide member to the cardiac lead allows the user to apply torque to the lead and the guide member to steer the cardiac lead system through the patient's anatomy.

FIG. 6A illustrates a cut away view of one illustrative embodiment of the cardiac lead system 600 comprising a cardiac lead 601 and guide member 620, wherein the cardiac lead 601 and the guide member 620 have compatible mating features 603, 604. FIGS. 6B and 6C illustrate cross sectional views of the guide member 620 and the cardiac lead 601, respectively. In accordance with this embodiment, a guide member 620 is displaceable within a multi-diameter cardiac lumen 606. The mating feature 604 of the cardiac lead 601 includes one or more slots or depressions 681, e.g., rectangular, wedge, or other type of slot for receiving and engaging compatibly shaped protrusions 682 of the mating feature 603 of the guide member 620. When the mating feature 603 of the guide member engages the mating feature 604 of the cardiac lead 601, the cardiac lead 601 and the guide member 620 may be concurrently rotated or torqued together to guide the cardiac lead system 600 through the patient's vasculature.

A first set of mating features may be positioned, for example, within the transition region of the cardiac lead lumen. The second set of mating features may be positioned, for example, within the transition region of the guide member or at the distal end of a hollow elongated body. Other locations for the mating features are also possible and are considered to be within the scope the invention.

The guide member may include a pre-shaped portion for facilitating insertion of the cardiac lead system. FIG. 7A illustrates a portion of the distal end of a guide member 720 having a guide wire extension 722 with a fixed pre-shaped curve 725 to assist the physician in steering the cardiac lead system into the desired vessel. Patient's exhibiting symptoms of advanced heart disease can have blockages or deformations of heart structure complicating the insertion of cardiac leads. Particularly in cases of patients with convoluted vasculature, a deflectable guide wire extension may be advantageous. An example of a deflectable guide wire extension using a moveable core is illustrated in FIG. 7B.

FIG. 7B illustrates a cut away view of a guide member 720 with a moveable core 727 displaceable within a lumen 726 of the guide member and extendable into the guide wire extension 722. In this example embodiment, the guide wire extension 722 has a preformed shape as described in connection with FIG. 7A. As the moveable core 727 is advanced into the guide wire extension, the pre-formed curve 725 of the guide wire extension 722 straightens, deflecting the distal tip 779 of the guide wire extension 722. The moveable core 727 may be retracted, allowing the guide wire extension 722 to return to its previous shape. The deflectable guide wire extension 722 may be particularly useful in moving the cardiac lead system through tortuous sections of the patient's vasculature.

The guide member having a pre-formed shape, illustrated in FIG. 7A, or the guide member having a moveable core, illustrated in FIG. 7B, may be used with any of the embodiments described in connection with FIGS. 1-6.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A cardiac lead system, comprising:
   a cardiac lead having an electrical conductor and a lumen extending from a proximal end of the lead to a distal external opening at a distal end of the lead, an electrode arrangement provided at the distal end of the lead;
   a guide member displaceable within the cardiac lead lumen, the guide member having a distal portion dimensioned to pass through the external distal opening of the cardiac lead lumen; and
   a stop mechanism, wherein activation of the stop mechanism causes locking engagement between the cardiac lead and the guide member, prevents further advancement of the guide member through the cardiac lead lumen, and facilitates transmission of torque applied to the lead and the guide member for steering the cardiac lead system through a patient's vasculature.

2. The cardiac lead system of claim 1, wherein the stop mechanism is positioned near a distal end of the cardiac lead system.

3. The cardiac lead system of claim 1, wherein the stop mechanism comprises an inflation member.

4. The cardiac lead system of claim 3, wherein the inflation member is positioned on the guide member.

5. The cardiac lead system of claim 1, wherein the stop mechanism comprises a clamp positioned near a proximal end of the cardiac lead system.

6. The cardiac lead system of claim 5, wherein the clamp is positioned external to a patient and is configured to attach a component of the guide member to a component of the cardiac lead upon activation.

7. The cardiac lead system of claim 5, wherein the stop mechanism fixed to at least one component of the guide member and is configured to attach the least one component of the guide member to a component of the cardiac lead upon activation.

8. The cardiac lead system of claim 7, wherein the stop mechanism is configured to attach the at least one component of the guide member to the guide wire.

9. The cardiac lead system of claim 1, wherein the guide member has a pre-formed shape.

10. The cardiac lead system of claim 1, wherein the guide member is deflectable.

11. The cardiac lead system of claim 1, wherein the guide member is solid.

12. The cardiac lead system of claim 1, wherein the guide member further comprises a lumen and moveable core accessible at a proximal end of the guide member, wherein advancing the moveable core through the lumen of the guide member causes a distal deflection of the guide member.

13. A cardiac lead system, comprising:
   a cardiac lead having an electrical conductor and a lumen extending from a proximal end of the lead to a distal external opening at a distal end of the lead, an electrode arrangement provided at the distal end of the lead;
   a guide member displaceable within the cardiac lead lumen, the guide member having a distal portion dimensioned to pass through the external distal opening of the cardiac lead lumen; and
   an inflation member, wherein activation of the inflation member causes locking engagement between an outer surface of the inflation member and an inner surface of the lumen of the cardiac lead, prevents further advancement of the guide member through the cardiac lead lumen, and facilitates transmission of torque applied to the lead and the guide member for steering the cardiac lead system through a patient's vasculature.

14. The cardiac lead system of claim 13, wherein the inflation member is positioned on the guide member, the inflation member dimensioned to engage an inner surface of the cardiac lead lumen upon inflation.

15. The cardiac lead system of claim 13, wherein the inflation member comprises an inflation balloon.

16. The cardiac lead system of claim 13, wherein the inflation member is in communication with an inflation lumen extending from a proximal end of the cardiac lead system.

17. The cardiac lead system of claim 13, wherein the guide member has a pre-formed shape.

18. The cardiac lead system of claim 13, wherein the guide member is deflectable.

19. The cardiac lead system of claim 13, wherein the guide member is solid.

20. The cardiac lead system of claim 13, wherein the guide member further comprises a lumen and moveable core accessible at a proximal end of the guide member, wherein advancing the moveable core through the lumen of the guide member causes a distal deflection of the guide member.

* * * * *